US00PP29212P3

(12) United States Plant Patent
Nakashima

(10) Patent No.: US PP29,212 P3
(45) Date of Patent: Apr. 10, 2018

(54) ROSE PLANT NAMED 'RNF PINK 01'

(50) Latin Name: ***Rosa* L.**
Varietal Denomination: RNF Pink 01

(71) Applicant: Kaneya Co., Ltd., Chita, Aichi (JP)

(72) Inventor: Hitoshi Nakashima, Gifu (JP)

(73) Assignee: Kaneya Co., Ltd., Aichi (JP)

( * ) Notice: Subject to any disclaimer, the term of this patent is extended or adjusted under 35 U.S.C. 154(b) by 2 days.

(21) Appl. No.: 14/999,305

(22) Filed: Apr. 21, 2016

(65) Prior Publication Data

US 2017/0311497 P1 Oct. 26, 2017

(51) Int. Cl.
*A01H 5/02* (2006.01)

(52) U.S. Cl.
USPC ..... Plt./107
CPC ..... *A01H 5/0222* (2013.01)

(58) Field of Classification Search
USPC ..... Plt./107
See application file for complete search history.

*Primary Examiner* — Keith O Robinson
(74) *Attorney, Agent, or Firm* — The Webb Law Firm

(57) ABSTRACT

A new and distinct rose plant having a strong fragrance and deep pink-colored flowers.

4 Drawing Sheets

Botanical classification: *Rosa* L.
Varietal denomination: 'RNF Pink 01'.

BACKGROUND OF THE INVENTION

The present invention comprises a new and distinct cultivar of rose plant known by the varietal name 'RNF Pink 01'. The new variety was discovered in April of 2010 in Gifu, Japan. The new variety is the result of a planned breeding program between a *Rosa* L. variety named 'Bridal Pink' (female parent, U.S. Plant Pat. No. 2,851) and an unnamed and unpatented *Rosa rugosa* variety (male parent) from the breeder's own collection. 'RNF Pink 01' is similar to its female parent in thorn shape and upright growth habit, but 'RNF Pink 01' has a deeper pink flower color, fewer thorns, and more buds per stem that bloom like a bunch that differentiate it from its female parent. Additionally, 'RNF Pink 01' exhibits a similar petal shape to its male parent, but differs from its male parent in its actual fragrance and the fact that 'RNF Pink 01' has an upright growth habit versus its male parent's spreading growth habit. When 'RNF Pink 01' is compared to *Rosa* L. 'Evera 186' (currently unpatented in the U.S., Japanese Patent No. 20884), the varieties are similar in that they both exhibit an upright growth habit and double flowers, but 'RNF Pink 01' has a slightly lighter pink flower color and different petal shape than 'Evera 186'. When generally compared to other rose varieties known to the breeder, the new variety differs in its strong fragrance, its type of fragrance, and in flower color. 'RNF Pink 01' has been trial and field tested and has been found to retain its distinctive characteristics and remain true to type through successive propagations.

DESCRIPTION OF THE DRAWINGS

The accompanying photographic drawings taken from 3-4 years of age illustrate the new variety, with the color being as nearly true as is possible with color illustrations of this type.

DESCRIPTION OF THE PLANT

Figure 1:
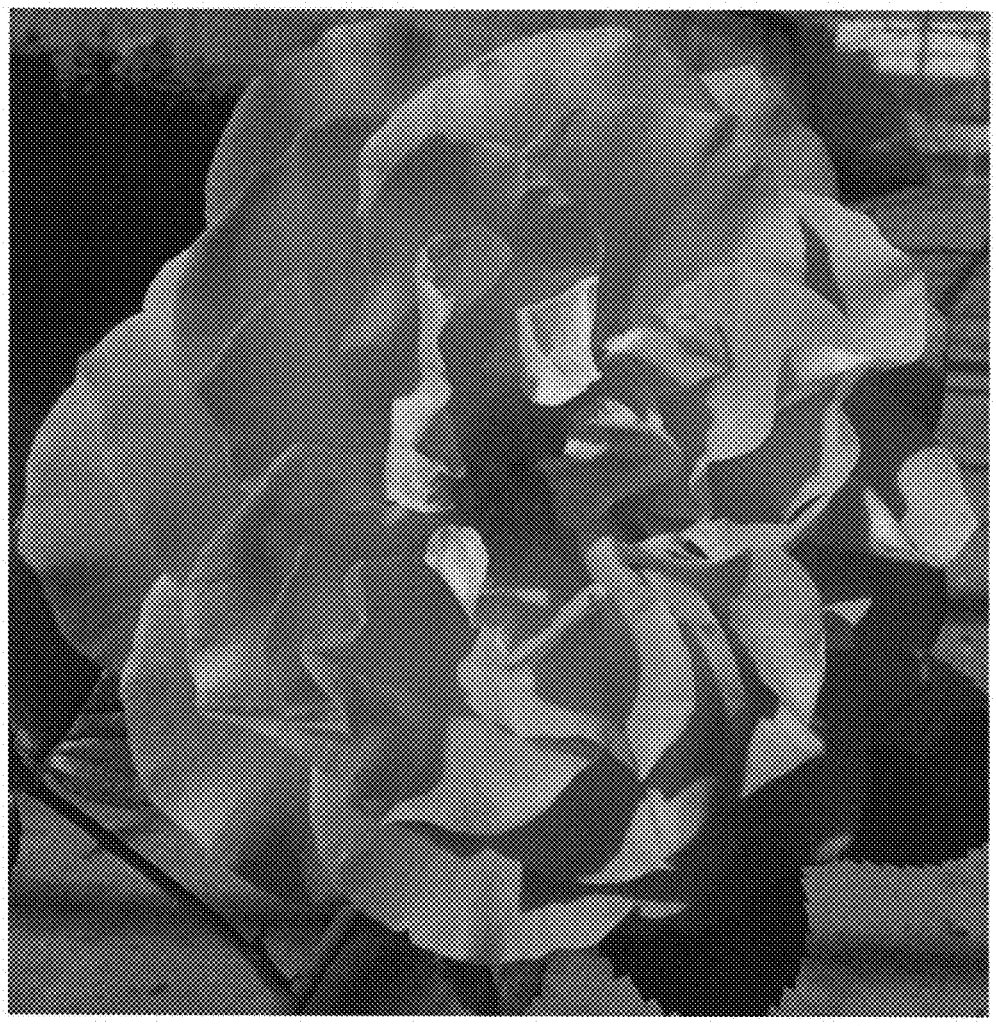
FIG. 1 shows a close-up view of a flower of the new variety.
Figure 2:
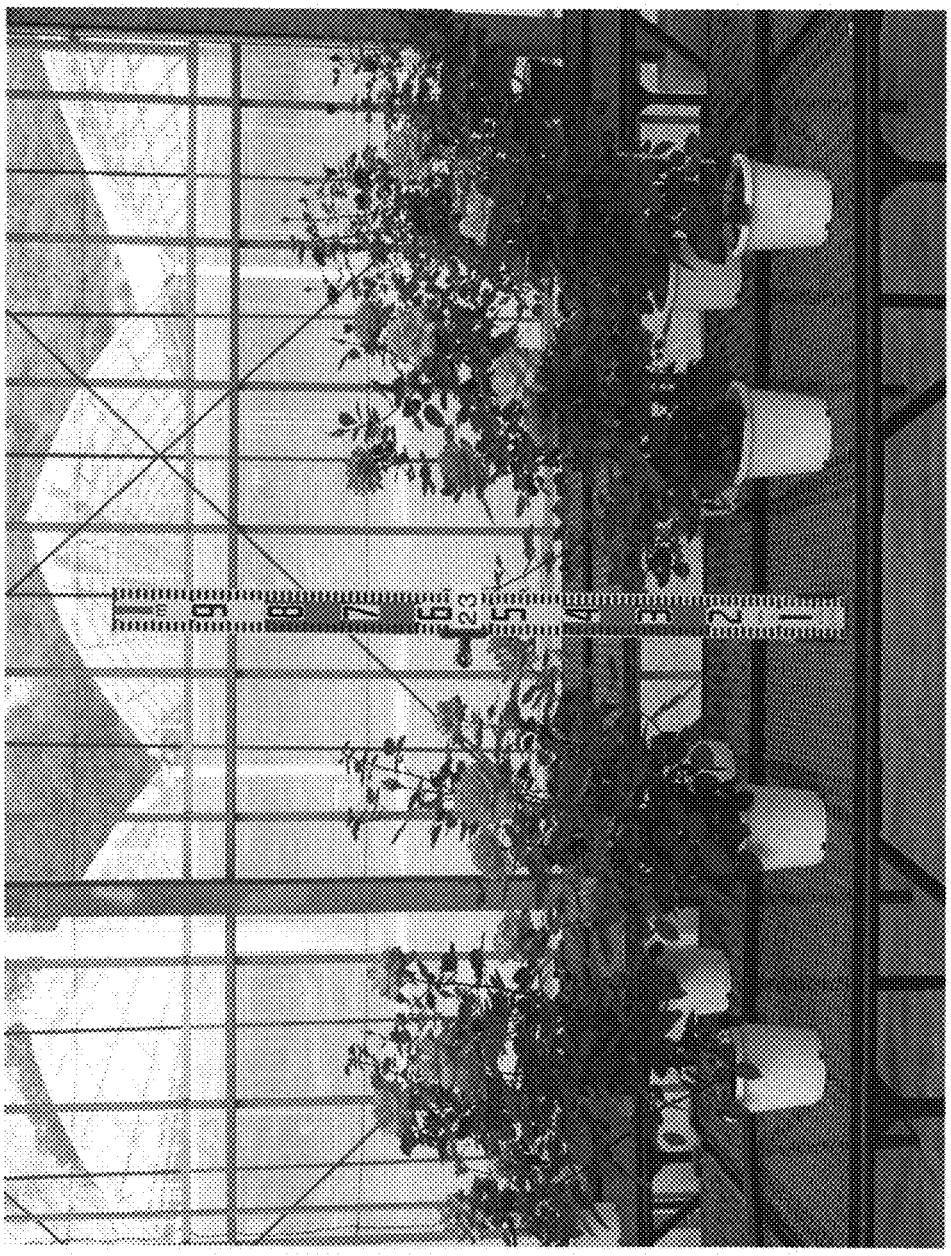
FIG. 2 shows a view of multiple plants of the new variety.
Figure 3:
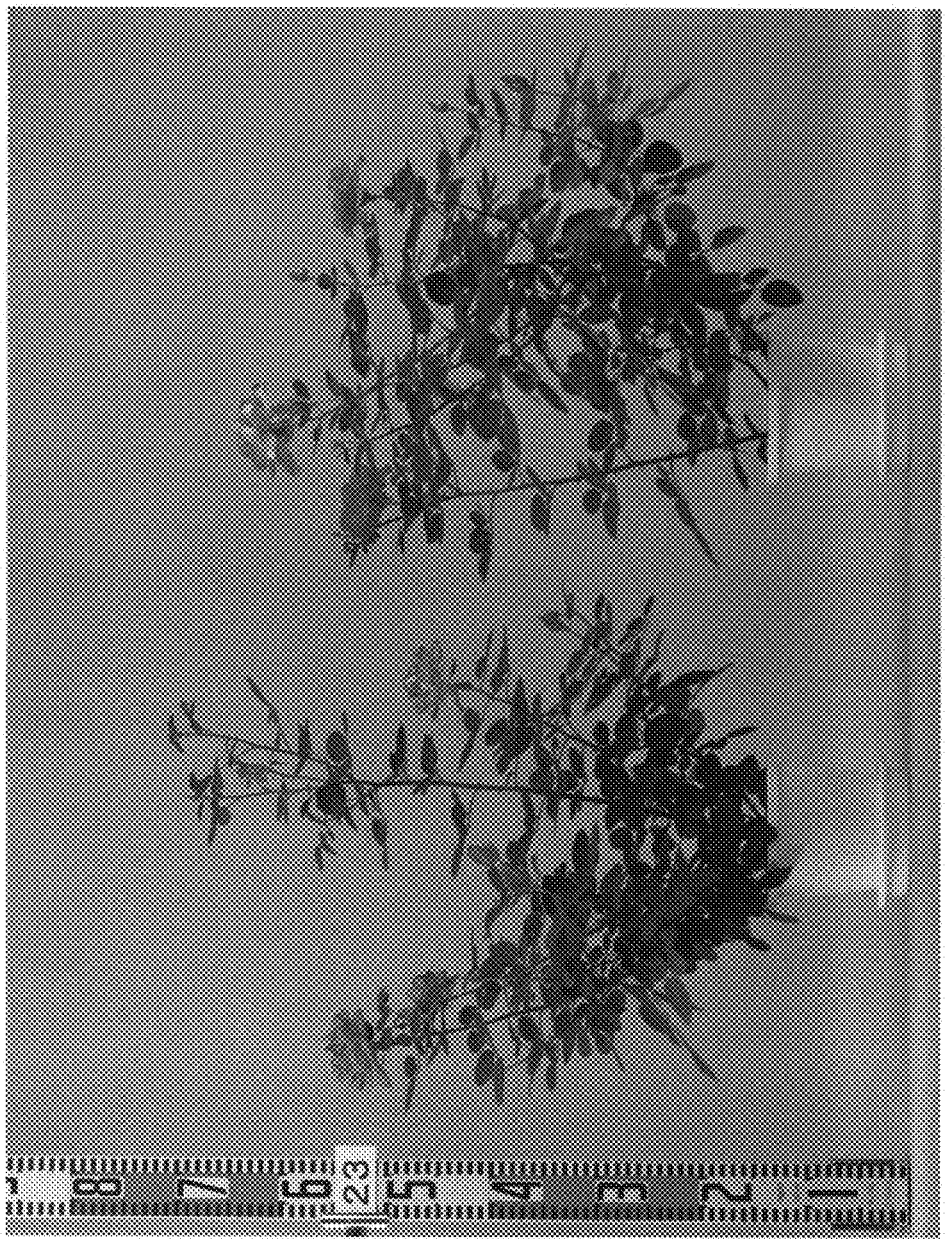
FIG. 3 shows a view of multiple plants of the new variety.
Figure 4:
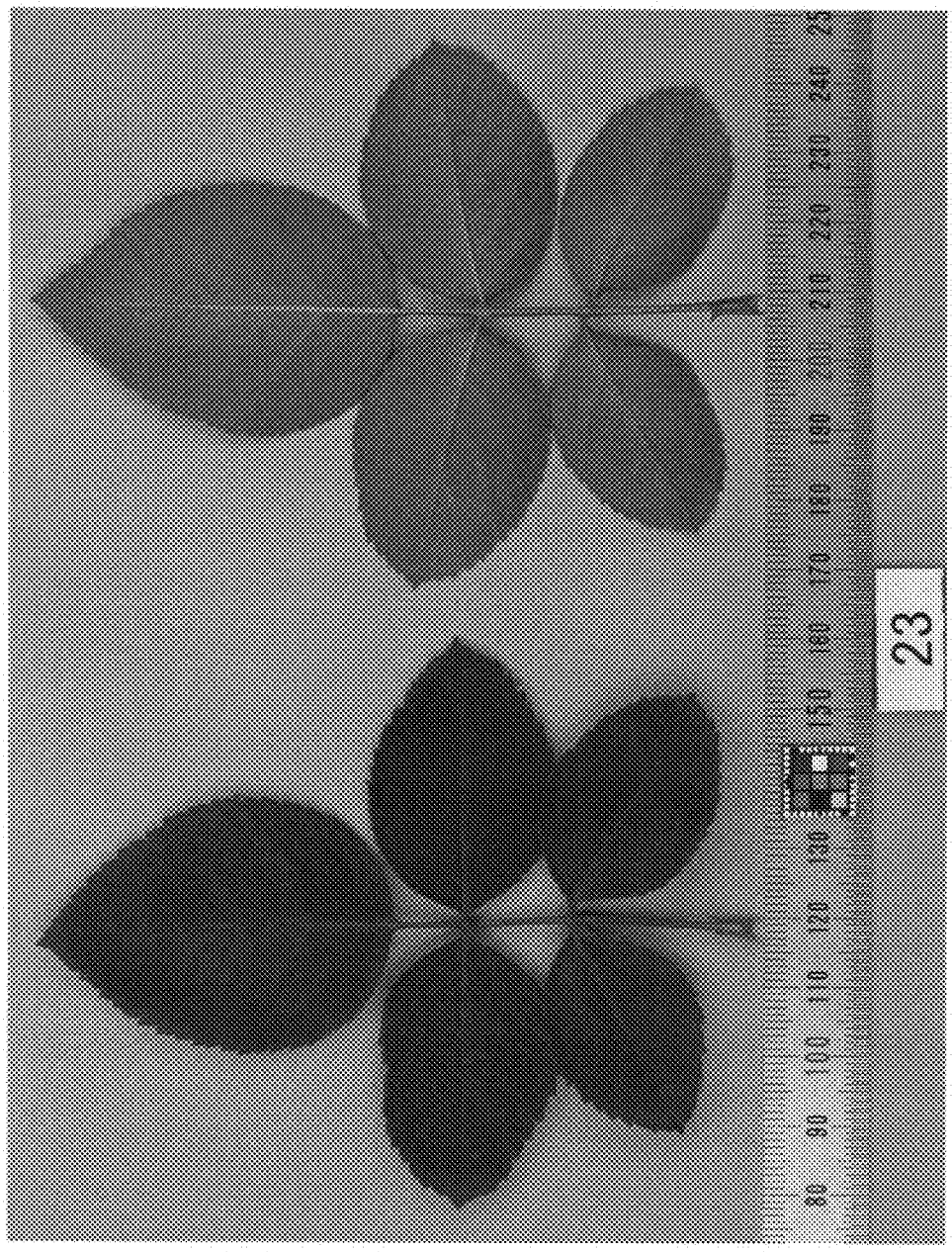
FIG. 4 shows the leaves of the new variety.

The following detailed description sets forth the characteristics of the new cultivar. The data which defines these characteristics were collected by asexual reproductions first performed via stem cuttings in May of 2011 carried out in Gifu, Japan. Plants of the new variety were grown in a greenhouse under natural light in 15 cm pots with peat moss substrate and with the assistance of heaters in the winter. The color readings and measurements were taken indoors in a greenhouse under natural light on one-year-old plants grown in containers. Color references are primarily to The 2015 R.H.S. Colour Chart of The Royal Horticultural Society of London, Sixth Edition.

PLANT

Time to initiate roots: About 21-28 days at approximately 25° C.

Time to develop roots: About 30-45 days at approximately 25° C.

Time to produce a finished flowering plant from a rooted cutting: About 5 months/20-22 weeks in a 15 cm container.

Rooting habit: Having a main root with lateral roots emerging therefrom.

Growth habit: Upright.

Distance from media surface to top of foliage: 30-35 cm at the end of production.

Distance from media surface to top of flowers: 35-40 cm.

Plant diameter: Around 25 cm.

Vigor: Average.

Strength (need for artificial support): No artificial support needed.
Branching characteristics: Branching from bottom or lower level.
Stem color:
*Immature*.—N57A.
*Mature*.—135D.
Surface texture:
*Young wood*.—Rough, with small thorns present.
*Older wood*.—Smooth and glossy.
Average stem diameter: From 7 mm to 1 cm.
Internode length: Approximately 4 to 5 cm.
Number of internodes: 6 to 7.
Thorns:
*Average number*.—Main branches: 70 per plant. Stems: 12 per stem.
*Length*.—7 mm to 1 cm.
*Width*.—Around 5 mm.
*Color*.—Ivory/beige to red (65A).
*Shape*.—Acuminate.
Foliage:
*Arrangement*.—Alternate.
*Average number of leaves per lateral branch*.—5.
*Average number of leaflets per leaf*.—5.
*Overall size of leaf*.—Length: 10 cm. Width: 5 cm.
*Leaflet*.—Shape of leaf (generally): Ovate. Shape of apex: Acute. Shape of base: Obtuse. Length range: 5-7 cm. Width range: 3-5 cm. Texture: Moist and wet, with weak glossiness on the upper surface. Margin type: Serrate. Color: Young leaves: Upper surface: 141C, with a 60B edge. Lower surface: 144C, with a 60B edge. Mature leaves: Upper surface: 132A. Lower surface: 135D. Veins: Venation type: Pinnate. Color: 135D.
*Petiole*.—Length: 2-3 mm. Diameter: 1-2 mm. Color: 135C. Texture: Rough.
*Stipule*.—None present.

INFLORESCENCE

Buds:
*Number of buds per plant*.—10.
*Number of buds per flowering stem*.—2.
*Shape of individual bud*.—Napiform.
*Length of individual bud*.—1.5-2 cm.
*Width of individual bud*.—8 mm to 1 cm.
*Bud color*.—143C.
Natural flowering season at specified location: End of April to May in Gifu, Japan.
Average number of flowers per year at specified location: 10 to 15.
Flowering habit: Continuous and freely flowering.
Flower description: 2 or more flowers and bloom like a bunch.
Lastingness of an individual flower on the plant: 10 days to 2 weeks.
Lastingness of a cut flower: 1 week.
Flower:
*General appearance*.—Double flowering rose.
*Shape*.—Round and mounded.
*Diameter*.—8-10 cm.
*Height*.—3-4 cm.
Petals:
*Color*.—Upper surface (when opening): 67C. Lower surface (when opening): 67C, with a bit of 49D. Upper and lower surfaces (fully opened): 67C.
*Shape*.—Rounded.
*Length*.—4-5 cm.
*Width*.—5-6 cm.
*Apex shape*.—Round with a wide lip.
*Base shape*.—Round and narrow.
*Margin*.—Entire.
*Number per flower*.—25-35.
*Texture*.—Soft.
*Reflex characteristics*.—None.
*Presence of basal petal spots*.—None.
*Petaloid description*.—Lightly fringed with semi-double flowering.
Sepals:
*Color*.—Upper and lower surfaces (when opening): 143B. Upper and lower surfaces (fully opened): NN137A.
*Shape*.—Sharp.
*Length*.—2-3 cm.
*Width*.—8 mm to 1 cm.
*Apex shape*.—Pointed.
*Base shape*.—Wide.
*Margin*.—Entire and tight, when closed.
*Number per flower*.—4-5.
*Texture*.—Rough.
Pedicel:
*Length*.—3-5 cm.
*Diameter*.—3 mm.
*Texture*.—Soft and smooth.
*Strength*.—Strong.
*Color*.—141D.
Peduncle color: 141D.
Receptacle:
*Texture*.—Hard and fluffy.
*Shape*.—Semicircle.
*Height*.—5-7 mm.
*Width*.—5-7 mm.
*Color*.—157A.
Fragrance: Strong.
Disease/pest resistance: Average resistance to powdery mildew of the Erysiphaceae family.
Winter temperature tolerance: Blooming at 1° C. in winter. With only roots, −15~−18° C.
Hot temperature tolerance: 40° C.
Drought tolerance: Average.
Reproductive organs:
Stamens:
*Number (per flower)*.—50.
*Filament*.—Length: 7-10 mm. Color: 157C.
*Anthers*.—Shape: Like a match stick. Length: 2-3 mm. Color: 183B.
*Pollen*.—Color: 12D. Amount (generally): Less than average.
Pistils:
*Number*.—50.
*Length*.—1-2 mm.
*Style*.—Length: Average. Color: 157C.
*Stigma*.—Shape: Funnel. Color: 157C. Size: 1 mm.
*Ovaries*.—Length: 3 mm. Width: 0.5 mm. Color: 157B.

I claim:

1. A new and distinct variety of rose plant, as is herein illustrated and described.

* * * * *